United States Patent [19]

Beljanski

[11] Patent Number: 5,567,593
[45] Date of Patent: Oct. 22, 1996

[54] CYTODIAGNOSTIC METHOD USING ALSTONINE AS A SELECTIVE MARKER, AND DIAGNOSTIC KIT CONTAINING MARKER

[76] Inventor: Mirko Beljanski, 46 Boulevard De Port Royal, 75005 Paris, France

[21] Appl. No.: 196,165

[22] PCT Filed: Jul. 26, 1993

[86] PCT No.: PCT/FR93/00762

§ 371 Date: Feb. 22, 1994

§ 102(e) Date: Feb. 22, 1994

[87] PCT Pub. No.: WO93/02829

PCT Pub. Date: Feb. 3, 1994

[30] Foreign Application Priority Data

Jul. 28, 1992 [FR] France .................. 92 09283

[51] Int. Cl.$^6$ .............. G01N 33/574; G01N 33/48; A01N 25/34

[52] U.S. Cl. .............. 435/7.23; 435/7.21; 435/39; 435/808; 435/810; 435/968; 436/63; 436/64; 436/164; 436/172; 436/805; 436/813; 436/816; 514/960; 514/962; 424/408

[58] Field of Search .............. 435/7.23, 7.21, 435/39.808, 810, 968; 436/63, 64, 164, 172, 805, 813, 816; 514/960, 962; 424/408

[56] References Cited

U.S. PATENT DOCUMENTS

| 4,160,019 | 7/1979 | Bjorklund | 424/12 |
|---|---|---|---|
| 4,755,684 | 7/1988 | Leuirer et al. | 250/461.1 |
| 5,015,463 | 5/1991 | Dougherty et al. | 424/7.1 |
| 5,283,255 | 2/1994 | Levy et al. | 514/410 |

FOREIGN PATENT DOCUMENTS

| 0059817 | 9/1982 | European Pat. Off. . |
|---|---|---|
| 2419725 | 10/1979 | France . |
| 2439783 | 5/1980 | France . |

OTHER PUBLICATIONS

Belzanski et al, *Exp. Cell Biol*, vol. 50, pp. 79–87 (1982).
Belzanski et al. *Oncology*, vol. 43, pp. 198–203 (1986).
Beljanski et al., "Three alkaloids as selective destroyers of the proliferative capacity of cancer cells", IRCS Medical Science 12: 587–588 (1984).
Beljanski et al., "Three alkaloids as Selective Destroyers of Cancer Cells in Mice", Oncology 43: 198–203 (1986).
Beljanski et al., "Selective Inhibition of in vitro synthesis of Cancer DNA by alkaloids of the β–Carboline Class", Exp. Cell Biol. 50:79–87 (1982).

*Primary Examiner*—Elizabeth C. Weimar
*Assistant Examiner*—Abdel A. Mohamed
*Attorney, Agent, or Firm*—Oppedahl & Larson

[57] ABSTRACT

An alstonine composition is useful as a selective marker of tumor cells and/or of chromosomal aberrations, and for the detection thereof by measurement of fluorescence at about 375 nm. Thus, an alstonine preparation can be used as a diagnostic agent designed for selective detection of tumoral diseases, and in cytogenetics. The diagnostic agent has application in preoperative, peroperative and postoperative diagnoses.

21 Claims, 4 Drawing Sheets

IF=Intensity of Fluorescence

CYTODIAGNOSTIC METHOD USING ALSTONINE AS A SELECTIVE MARKER, AND DIAGNOSTIC KIT CONTAINING MARKER

The present invention relates to cytodiagnostic techniques. More particularly, it relates to the detection of tumors, notably for the establishment of a tumoral diagnosis, and to the detection of chromosomal aberrations by means of alstonine, using a procedure of selective detection by fluorescence.

In the present description, the term "cytodiagnostic" is understood to include both the diagnosis of tumoral diseases and cytogenetics.

Alstonine is an alkaloid extracted from *Rauwolfia vomitoria*, *Rauwolfia obscura* and *Vinca rosea*, as well as from other Apocyanaceae. It belongs to the group of quaternary beta-carbolines. Methods of extraction of this alkaloid have been described by M. Beljanski and J. Bugiel in French Patent Publication FR-A-78 30663 and European Patent Publication EP-A-0 059 817, whose content is incorporated herein by reference. It has also been shown that this alkaloid has a very vivid pale blue fluorescence, which on spectrophotometric analysis corresponds to two absorption maxima, at 252 and 308 nm, respectively, which are characteristic of alstonine and of its isomer serpentine.

It has also been shown, notably in the above-mentioned documents, that alstonine has anti-cancerous properties. These properties are now well substantiated on mouse YC8 lymphoma ascites cells; on Ehrlich "ascites" tumor cells in mice; on type KB, HELA, HEPII and L cancer cell cultures; and on cells originating from nephroblastoma, neuroblastoma or teratoma, all of which are human tumors, primary cultures of which alstonine was found to destroy completely within 24 to 48 hours. By way of comparison, in order to firmly establish the selectivity of action of alstonine against cancerous cells, the same alstonine dose (200 mcg per ml of culture) was applied to primary cultures of monkey kidney cells or to Vero or Circ-type cell lines; in these cases, it produced no cellular destruction within 8 days. This proved the specific interaction of alstonine with the DNA of tumor cells, whereas the DNA of normal cells was not affected by this alkaloid.

However, it was still difficult to have good control of an antitumor treatment using such an alkaloid and/or to establish a reliable diagnosis of a patient's condition in the preoperative, peroperative and post-operative stages. Hence, there was a need for a means for the evaluation of tumoral diseases in order to facilitate the diagnosis of cancerous lesions and of metastases, and to improve their treatment.

SUMMARY OF THE INVENTION

It has now been unexpectedly found that alstonine itself, can be used to obtain a selective diagnosis of tumoral diseases both with regard to their location and to provide an estimate of their size. It has also been found that a similar alstonine composition is useful in cytogenetics. Thus, in accordance with the invention, a method is provided for the detection of tumor cells or of chromosomal aberrations in a tissue sample, comprising treating the tissue sample with a composition comprising alstonine or an isomer thereof, irradiating the treated tissue sample with light having a wavelength effective to induce a fluorescent emission at about 446 nm from alstonine absorbed into tumor cells or cells having a chromosomal aberration; and detecting any fluorescence from the tissue sample. This method can be used for both in vivo and in vitro diagnoses.

The invention also relates to kits for performing cytodiagnostic evaluations on tissue samples in accordance with the method of the invention. Such a kit includes (a) a composition comprising alstonine or an isomer thereof at a concentration effective to impart measurable fluorescence to tumor cells or to cells having chromosomal aberrations, and (b) an incubation support adapted for incubation of the tissue sample in the composition.

The invention further relates to an article of manufacture comprising a packaging material and a cytodiagnostic agent contained within said packaging material, wherein said cytodiagnostic agent comprises alstonine or an isomer thereof at a concentration effective to impart a detective level of fluorescence to tumor cells, and wherein said packaging material comprises a label which indicates that said cytodiagnostic agent can be used for the detection of tumors and chromosomal aberrations. In one embodiment, the cytodiagnostic agent is provided as a galenic preparation in the form of a tablet or capsule for oral administration.

BRIEF DESCRIPTION OF THE DRAWINGS

The invention is described below in greater detail by reference to the appended figures, wherein.

DETAILED DESCRIPTION OF THE INVENTION

The present invention takes advantage of the facts that alstonine and its isomer serpentine accumulate in tumor cells, or cells having chromosomal aberrations, but not in normal cells, and can be detected by fluorescence measurements. Thus, tumor cells or cells having chromosomal variations can be distinguished from normal cells for cytodiagnostic purposes by treatment with alstonine and observation of the treated cells for fluorescence at a wavelength characteristic of alstonine.

Figure 1:
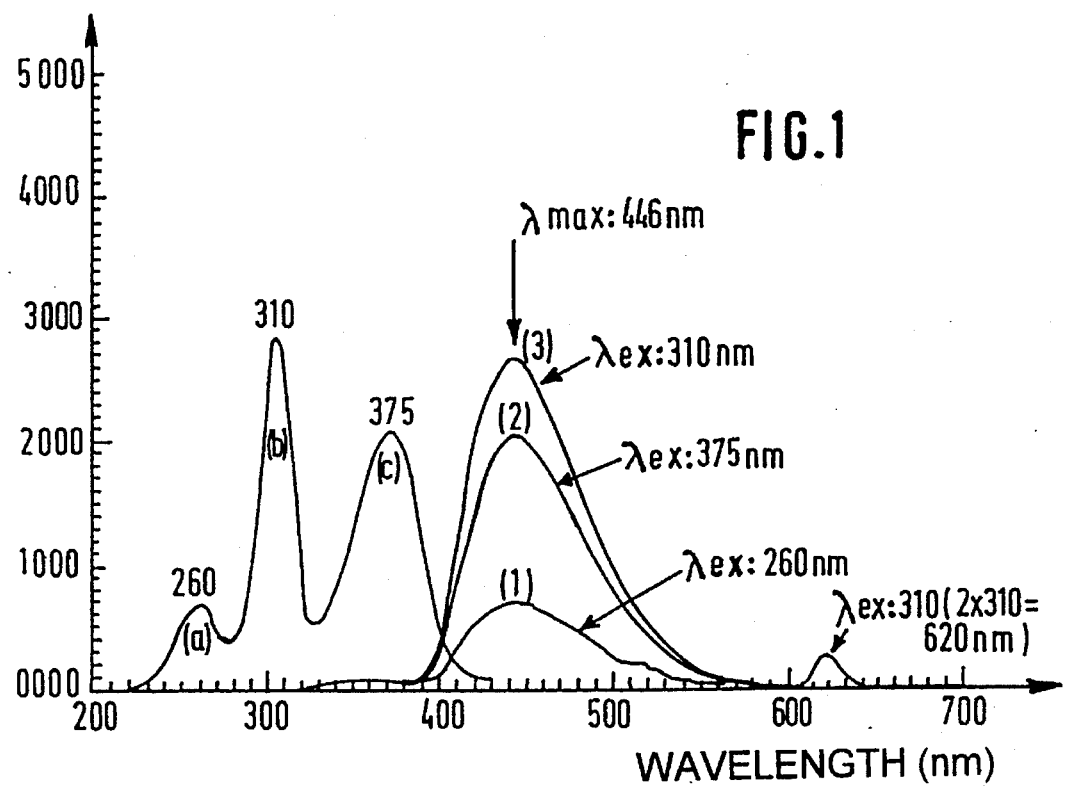
FIG. 1 shows the excitation and emission spectra of alstonine.
Figure 2:
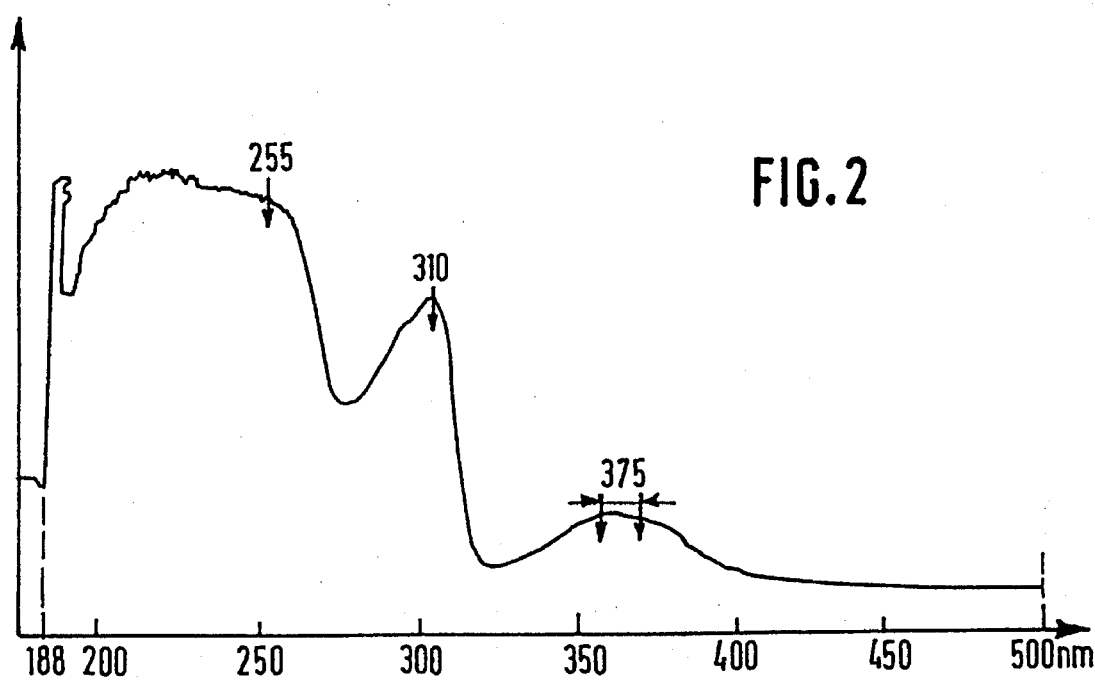
FIG. 2 shows the absorption spectrum of alstonine.

As shown in FIG. 1, which shows the excitation and emission spectra of a $5 \times 10^{-6}$M solution, alstonine excited at the three wavelengths of 260, 310 and 375 nm produces fluorescence in the visible range (446 nm) with quantum yields which differ from one maximum to the other. The strongest emission corresponds to the excitation maximum at 310 nm. The UV absorption spectrum showed three absorption bands at about 260, 310 and 320 nm, respectively. (FIG. 2)

The quantum yield, which measures the ratio of emitted intensity to excitation intensity, makes it possible to classify the fluorescence excitation maxima according to their efficiency. The maximum efficiency is obtained at an excitation at 310 nm; the yield is lower but still very similar at 375 nm; by contrast, it is very low at an excitation wavelength of 260 nm. Because of the usual light absorption properties shown by optical fibers, an excitation wavelength of 260 nm would be unsuited for use with a conventional endoscope. Similarly, using an excitation wavelength of 310 nm is generally not compatible with most fluorescence instrumentation, because the glasses employed in fluorescence detection apparatus are transparent only above 360 nm. Hence, it is the existence of an efficient excitation wavelength at 375 nm that makes the present invention involving detection of alstonine by fluorescence feasible with existing equipment.

Figure 3A:
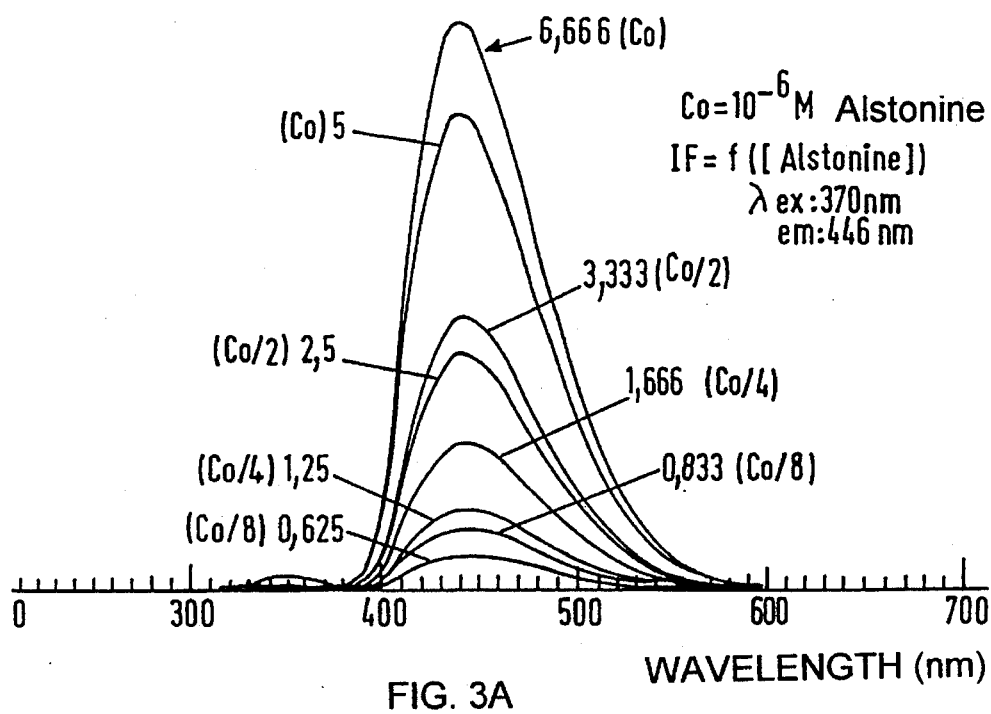
FIG. 3A shows the variation of the intensity of fluorescence as a function of the alstonine concentration.
Figure 3B:
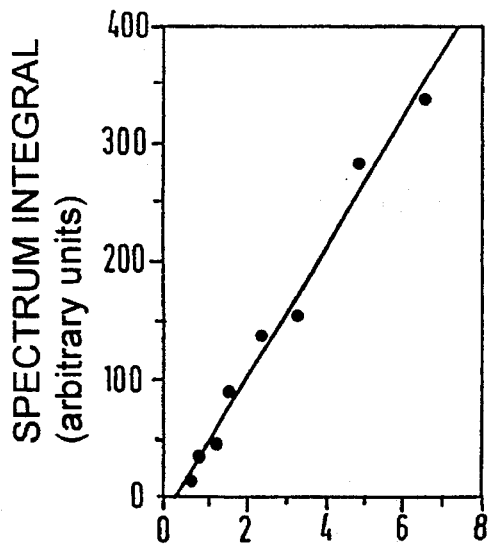
FIGS. 3B and 3C are plots showing that this variation is linear in the alstonine concentration range of from $10^{-6}$ to $10^{-5}$.
Figure 3C:
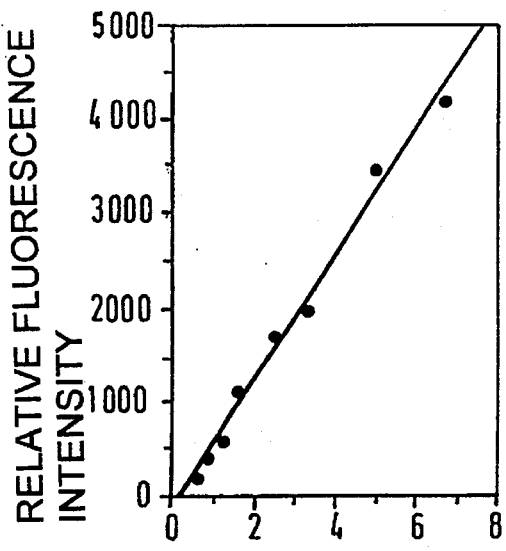
Figure 4A:
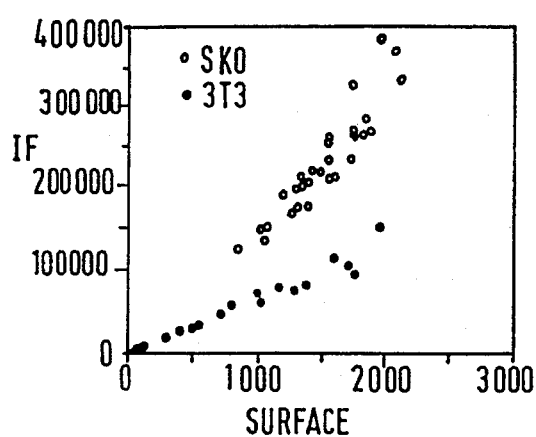
FIGS. 4A to 4D show the results of the analysis of certain physical-chemical parameters of alstonine incubated in accordance with the invention in the two cell populations SK0 and ST3, carried out by means of a fluorescence imaging analyzer.
Figure 4B:
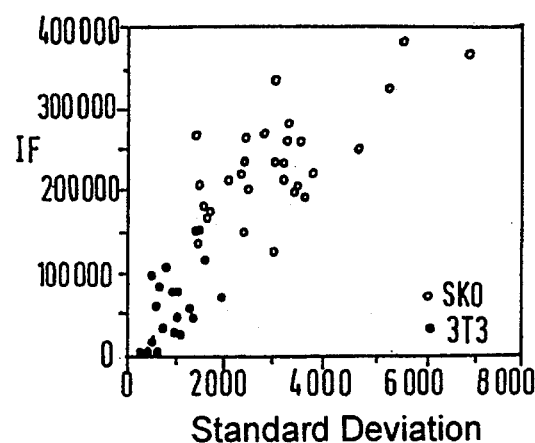
Figure 4C:
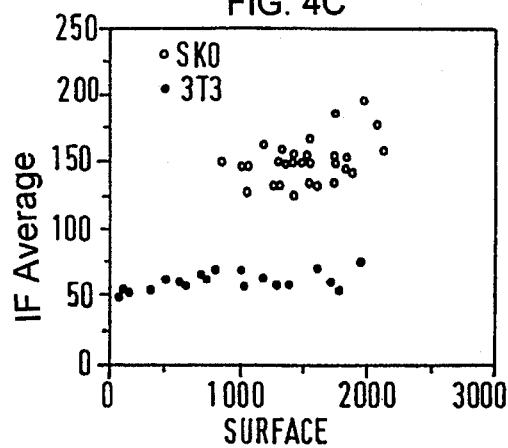
Figure 4D:
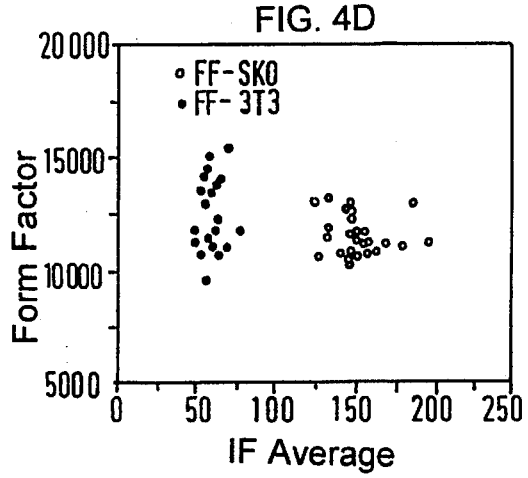

Furthermore, it was established that at constant excitation intensity a linear relationship exists between the intensity of fluorescence and the alstonine concentration. As indicated by the results shown in FIGS. 3A to 3C, at constant excitation intensity, the intensity of fluorescence of alstonine and the concentration of this alkaloid are in a linear relationship in an alstonine concentration range suitable for detection by instruments conventionally used in spectrofluorometry. This was found to be true particularly in an alstonine concentration range sufficient for the detection of alstonine but low enough so as to minimize the toxicity risks of the product with regard to healthy cells.

Figure 5A:
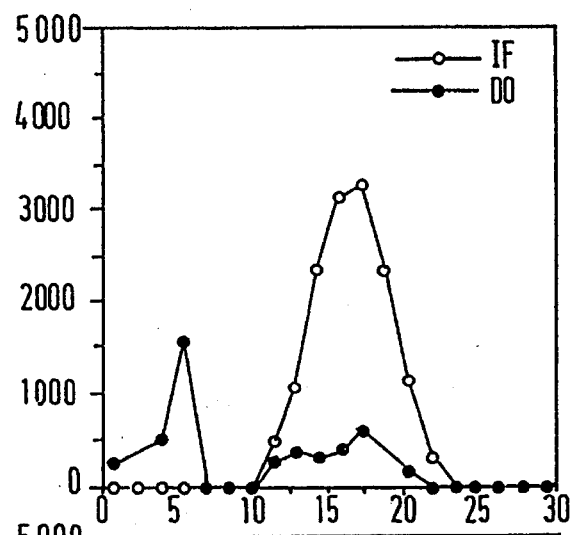
FIGS. 5A to 5C are diagrams showing the results of a Sephadex gel chromatography, using 10 mM tris-HCl buffer, pH 7.5, as eluent.
Figure 5B:
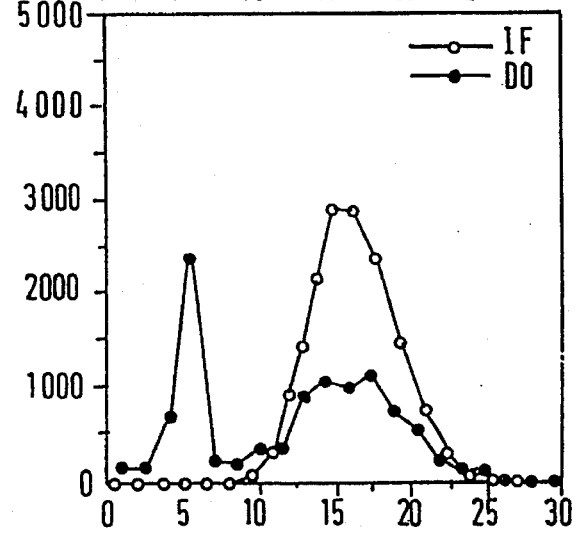
Figure 5C:
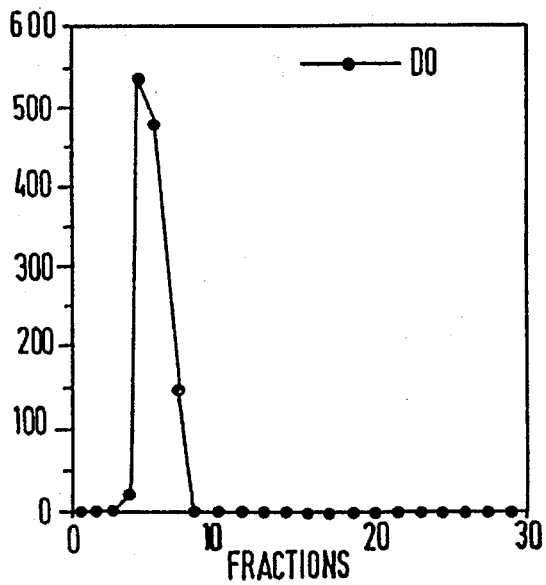

Studies carried out by chromatography on Sephadex gel columns (FIGS. 5A to 5C) showed that there is no interaction between the double-stranded DNA or single-stranded DNA isolated from normal cells and alstonine. These results are in agreement with the publications on alstonine which specify that the latter accumulates only in tumor cells, due to its interaction with tumoral DNA [on this subject see, in particular, M. Beljanski and M. S. Beljanski, *Exp. Cell. Biol.*, S. Karger AG, Basel, Pub. 50: 79–87 (1982), and M. Beljanski and M. S. Beljanski, *Oncology*, S. Karger AG, Basel, Pub. 43: 198–203 (1986)].

With regard to the alstonine accumulation studies conducted on live cell cultures of both normal cells (ST3) and tumor cells (SK0), they show (FIGS. 4A to 4D) that after incubation for about 20 minutes or more in the presence of the product, the fluorescence studies carried out with a Samba 2000 imaging analyzer detect a major accumulation only in the SK0 cells.

This accumulation of alstonine can be used in accordance with the invention to detect tumor cells in a tissue sample in vitro. The tissue sample is incubated in a composition containing alstonine, e.g., alstonine in aqueous solution at a concentration of about 0.2 to 5 mg per 20 ml of water, i.e. at a concentration of about 1 to 25% w/v. The incubation is advantageously done over a period of about 20 to 40 minutes at ambient temperature.

In in vitro applications, once this incubation stage has been completed, the tissue sample is rinsed with alcohol, preferably methanol, and a reading is made by irradiating the incubated sample and observing any fluorescence, for example with the fluorescence microscope.

For the preparation of a diagnostic kit usable mainly in in vitro tests, it is recommended to employ, as raw material, a purified saturated aqueous solution of alstonine, and to prepare, at the time of use, dilutions of this same solution in pure water for analyses at useful concentrations, which, in practice, range between about 5 and 10% w/v.

For application of the method of the invention in vivo, it is recommended to administer the alstonine in an appropriate galenic formulation, comprising suitable conventional pharmaceutical carriers or supports and possible excipients, for example, a form such as tablets or gelatin capsules advantageously containing about 3 to 500 mg of alstonine per unit dose is suitable. The administration is effected by the oral route t.i.d. on the day before the invivo diagnostic exploration.

For clinical use of alstonine and its isomers in accordance with the invention, notably in preoperative, peroperative and/or postoperative diagnosis and in the diagnosis of cutaneous diseases in confirmation of other examinations, it is recommended to detect the fluorescence under Wood's lamp excitation. This luminescence under Wood's lamp is utilized either by direct illumination or by transmission, notably by optical fibers in the case of endoscopic explorations.

As a variant to the detection of tumor cells, an alstonine composition can also be advantageously used according to the invention in cytogenetics, notably in investigations of an aberrant chromosome identification, through the detection, on the chromosomal level, of breaks, modifications and/or recombinations. In practice, this identification of chromosomal aberration, characteristic of a hereditary genetic disease, is effected through a specific luminescence band of one or more chromosomes involved in said chromosomal aberration and detected by the technique of the present invention.

As an example, diagnostic studies based on an alstonine composition in accordance with the invention and performed according to appropriate biological test protocols, have provided cytogenetic confirmation of the correlations between the loss of one of the two sex chromosomes and the establishment of solid tumors or malignant blood diseases: In the case of female subjects, the karyotype then becomes 45×0 by loss of a chromosome X;
In the case of male subjects, the karyotype then becomes 45×0, by loss of a chromosome Y.

The mechanism of cytogenetic action controlling these events may thus be evaluated qualitatively and quantitatively by differential coloration and lymphocyte culture studies, which make it possible to demonstrate the bridges and breaks and the recombinations.

Although the above description and the following illustrative examples make reference to alstonine as a particular alkaloid, persons skilled in the art will readily see that comparable results may be obtained if this alkaloid is totally or partially replaced by any equivalent technique for the use under consideration, notably by its isomer serpentine.

EXAMPLES OF USE FOR A DIAGNOSIS
BASED ON BIOLOGICAL SPECIMENS

Example 1

Various biological specimens were impregnated with an aqueous solution of alstonine containing about 200 micrograms of alstonine per milliliter; these specimens were incubated for 20–40 minutes, then subjected to microscopic examination under a Wood's lamp microscope.

Treated and examined in this manner was a smear of uterine cervix specimen on a glass slide, and the cancerous nature of the cellular elements was demonstrated by the luminescence observed under the Wood's lamp microscope.

Example 2

The procedure described in Example 1 was applied to a bone marrow smear on a glass slide.

The luminescence observed under the Wood's lamp microscope revealed the cancerous nature of the cellular elements.

Example 3

Proceeding as in Example 1 with a gastric specimen centrifuged and then spread on a glass slide, the presence of tumor cells was demonstrated by the luminescence of the smear on the slide, detected by the selective method of the invention.

Example 4

Proceeding as in Example 1, with a vesical specimen spread on a glass slide, the presence of tumor cells was demonstrated by the luminescence of the smear on the slide detected by the selective method of the invention.

The means and method according to the present invention are also useful for in-vitro cytogenetic detection of chromosomal aberrations linked with a hereditary genetic disease, this detection being effected by identification of a specific luminescence band of one or more chromosomes involved in breaks, modifications or recombinations.

EXAMPLES OF CLINICAL USE

Example 5

On the day before the diagnostic exploration, one gelatin capsule containing 250 mg of alstonine, prepared as indicated above, was orally administered t.i.d. at more or less equal intervals during the day, to patients in whom ovarian or vesical tumors were to be investigated and evaluated. Endoscopic examination done on the day following the administration of the capsules, with transmission through the endoscope of UV excitation radiation generated by a Wood's lamp, made it possible to confirm that the detection of neoplastic tumors was easy by this method. It was also established that the differential diagnosis with cancerous tumors was confirmed by biopsy and anatomopathologic examination.

Example 6

According to the procedure indicated in Example 5, a diagnosis of pancreatitis with development of a Weber-Christian type of extrapancreatic vasculitis was made in patient Mr. A. G., showing a torpid course for 10 years. In this way it was significantly verified that the consolidation did in fact occur after these ten years.

Example 7

According to the method indicated in Example 5, the diagnosis of a Merkel tumor was confirmed in a 74-year-old woman; this diagnosis was also confirmed by histological analyses of the excision of an APUD-type neuro-endocrine carcinoma tumor.

Example 8

According to the procedure indicated in Example 5, a generalized ichtyosis was detected under UV in young S. L. aged 8 years; in this way the presence of a thick keratosis without oligophrenia was noted. On subsequent repetition of the investigation according to the invention, the improvement resulting from the treatment was confirmed, as reflected by clearing of the face, lower limbs and upper limbs, but with persistence of the ichtyosis on the scalp, abdomen, chest and back.

Example 9

Using the procedure described in Example 5, a senile-type facial epitheliomatosis with development toward a right frontal basal cell formation was analyzed and located in a patient. On repeating the investigations of the present invention at suitable time intervals, the effects of the treatment administered were followed until filling up of the basocellular formation and its cicatrization.

Example 10

The procedure described in Example 5 was used in patient Mr. C. Y. presenting a cutaneous lymphoma of the type of Sesary's disease. During UV exploration after administration of alstonine under the conditions indicated in Example 1, this patient presented a lymphoid infiltration of the face of the leontiasis type, as well as zones of dermoepidermitis and pseudoplaques of leukodysplasia of the face and lips.

Example 11

In patient Mr. D. F., subjected to the same procedure as described in Example 5, the marking action of alstonine under UV revealed the existence of a recurrent fibrosarcoma after failure of its treatment at a time five years before this observation under UV. Monitoring of the treatment with alstonine under UV showed disappearance of the cicatricial luminescence, which demonstrated the recovery of the normal tissue at the tumor site.

Example 12

Using the procedure described in Example 5, the existence of a rectosigmoid adenocarcinoma was established and visualized by the fluorescence of alstonine in patient Mr. K., in whom this diagnosis was confirmed by the anatomopathologic study of the excision of a recurrent villose lesion, showing, in particular, the presence of a Stage I proliferative adenocarcinomatous focus.

Example 13

Using the procedure of Example 5 and after total gastrectomy in patient Mr. A. J. due to the existence of a neoplastic mass at the lesser curvature of stomach and celiac lymphnode chain, the luminescence of the surgical specimen made it possible to establish the topography of the hyperluminescent zones, corresponding to the sites of neoplastic ulcerations of the lesser vertical curvature.

Example 14

Proceeding as described in Example 5, patient Mrs. E. Y., who subsequently underwent laparotomy after ultrasonic exploration, showed, thanks to the luminescence of alstonine after the laparotomy, the existence of intensive luminescence over one ovary, and it was verified that the patient in effect suffered from a metastatic proliferation of a primary breast tumor.

Example 15

Proceeding as in Example 5, patient Mr. G. M. was treated by contact cobalt therapy for a spinocellular tumor of the ala nasi. The luminescence of alstonine made it possible to demonstrate the recurrence of dysplasia nasoorbital modifications on the opposite site (ricochet effect).

Comparable trials carried out with other betacarbolines having equivalent fluorescence properties, mainly with serpentine, have yielded similar results and thus constitute techniques equivalent to alstonine within the framework of the present invention.

The means according to the invention are thus remarkably useful for cytodiagnosis, which comprises the evaluation of tumoral diseases and cytogenetics. In vivo, they make it possible, with a precision and ease that have never been attained so far, to locate a tumor in the preoperative stage; in the peroperative stage, to make a study of the cancerous lesions and metastases thanks to the fluorescence; and in the postoperative stage to verify, by fiber endoscopy, whether metastases appear or progress after an anticancer treatment or chemotherapy using traditional methods.

I claim:

1. A method for the detection of tumor cells or of chromosomal aberrations in a tissue sample, comprising treating the tissue sample with a composition comprising alstonine or an isomer thereof, irradiating the treated tissue sample with light having a wavelength effective to induce a fluorescent emission having a wavelength of about 446 nm from alstonine absorbed into tumor cells or cells having a chromosomal aberration; and detecting any fluorescence from the tissue sample.

2. A method according to claim 1, wherein the irradiating light has a wavelength of about 375 nm.

3. A method according to claim 1, wherein the composition comprises alstonine in an aqueous solution at a concentration of 1 to 25% by weight per volume.

4. A method according to claim 1, further comprising the step of diluting a purified saturated aqueous solution of alstonine at the time of use, to form a composition for treating the tissue sample having an alstonine concentration of between about 5 and 10% by weight per volume.

5. A method according to claim 1, wherein the composition further comprises serpentine.

6. A method according to claim 1, wherein the irradiation is supplied by a Wood's lamp which emits at about 375 nm.

7. A method according to claim 1, wherein the irradiation is supplied by a fluorescence microscope which emits at about 375 nm.

8. A method according to claim 1, wherein the composition is in the form of tablets or gelatine capsules.

9. A method according to claim 8, wherein the composition contains 3 to 500 mg of alstonine per unit dose, and further comprises a conventional pharmaceutical support or carrier, and an excipient.

10. A method according to claim 1, wherein the tissue sample is treated in vivo in a patient, whereby the composition acts as a cytodiagnostic agent designed for the selective detection of tumoral diseases.

11. A method according to claim 10, wherein the composition is administered orally to the patient.

12. A method according to claim 1, wherein the tissue sample is treated in vitro.

13. A method according to claim 12, wherein the tissue sample is treated by incubating in the composition for a period of 20 to 40 minutes at ambient temperature.

14. A method according to claim 13, wherein the tissue sample is incubated in an aqueous solution containing about 200 µg of alstonine per ml.

15. A method according to claim 14, wherein the irradiation is supplied by a Wood's lamp which emits at about 375 nm.

16. A kit for diagnosis of tumoral diseases and/or of chromosomal aberrations in a tissue sample, comprising in packaged combination (a) a composition comprising alstonine or an isomer thereof at a concentration effective to impart measurable fluorescence to tumor cells or to cells having chromosomal aberrations, and (b) an incubation support adapted for incubation of the tissue sample in the composition.

17. A kit according to claim 16, further comprising a container of an alcoholic wash solution.

18. A kit according to claim 16, wherein the composition is a saturated aqueous solution of alstonine.

19. An article of manufacture comprising a packaging material and a cytodiagnostic agent contained within said packaging material, wherein said cytodiagnostic agent comprises alstonine or an isomer thereof at a concentration effective to impart a detectable level of fluorescence to tumor cells, and wherein said packaging material comprises a label which indicates that said cytodiagnostic agent can be used for the detection of tumors and chromosomal aberrations.

20. An article according to claim 19, wherein the cytodiagnostic agent comprises alstonine or an isomer thereof at a concentration of from 1 to 25 weight % per volume.

21. An article according to claim 20, wherein the cytodiagnostic agent is a galenic preparation in the form of a tablet or capsule.

* * * * *